United States Patent [19]

Buttimore

[11] 4,032,323

[45] June 28, 1977

[54] ISOTHIAZOLE DERIVATIVES

[75] Inventor: David Buttimore, Leigh-on-Sea, England

[73] Assignee: May & Baker Limited, England

[22] Filed: May 19, 1975

[21] Appl. No.: 578,870

Related U.S. Application Data

[60] Continuation of Ser. No. 417,192, Nov. 19, 1973, Pat. No. 3,922,160, which is a division of Ser. No. 241,833, April 6, 1972, abandoned.

[30] Foreign Application Priority Data

Apr. 7, 1971   United Kingdom .............. 9019/71

[52] U.S. Cl. ............................ 71/90; 260/247.1 M; 260/306.8 A; 424/270

[51] Int. Cl.$^2$ ..................................... C07D 275/02

[58] Field of Search ............ 260/306.8 A, 247.1 M; 71/90, 3; 424/270

[56] References Cited

UNITED STATES PATENTS

| | | | |
|---|---|---|---|
| 3,541,108 | 11/1970 | Schmidt et al. | ......................... 71/90 |
| 3,922,160 | 11/1975 | Buttimore | ................... 260/306.8 A |

*Primary Examiner*—R. J. Gallagher
*Attorney, Agent, or Firm*—Stevens, Davis, Miller & Mosher

[57] ABSTRACT

Isothiazoles with an alkyl substituent in the 3-position, a cyano group in the 4-position, and a grouping —NHCONR$^3$R$^4$ in the 5-position, R$^3$ and R$^4$ each being methyl or ethyl, possess herbicidal properties against dicotyledonous and monocotyledonous weeds.

16 Claims, No Drawings

ISOTHIAZOLE DERIVATIVES

This application is a continuation of my prior application Ser. No. 417,192 filed Nov. 19, 1973, now U.S. Pat. No. 3,922,160 granted Nov. 25, 1975, which in turn is a division of my earlier application Ser. No. 241,833, filed Apr. 6, 1972, and now abandoned. See also my prior application Ser. No. 489,250, filed July 17, 1974, now U.S. Pat. No. 3,890,131 granted June 17, 1975.

This invention relates to isothiazole derivatives which are of use as herbicides.

As a result of research and experimentation, it has been found that the isothiazole derivatives of the general formula:

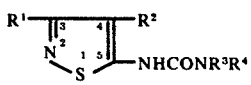

[wherein $R^1$ represents a straight- or branched-chain alkyl group containing from 1 to 3 carbon atoms, $R^2$ represents an alkoxycarbonyl group (wherein the alkoxy moiety is straight- or branched-chain and contains from 1 to 5 carbon atoms) or a cyano group, and when $R^2$ represents an alkoxycarbonyl group $R^3$ represents a hydrogen atom and $R^4$ represents a straight- or branched-chain alkyl or alkenyl group containing up to 5 carbon atoms, or a cyclopropyl group; and when $R^2$ represents a cyano group $R^3$ and $R^4$, which may then be the same or different, each represent a methyl or ethyl group] and salts of compounds of formula I, wherein $R^2$ represents a cyano group and $R^1$, $R^3$ and $R^4$ are as hereinbefore defined, with alkali metals, e.g. sodium or potassium, or strong organic bases, e.g. diethanolamine, triethanolamine or morpholine, possess useful herbicidal activity. It is to be understood that where in this specification reference is made to the compounds of general formula I, it is intended to refer also, where the context so permits, to the said salts of those compounds of general formula I wherein $R^2$ represents a cyano group, more particularly in respect of the use of the compounds as herbicides and herbicidal compositions therefor.

According to the present invention, at least one of the compounds of general formula I is used to control the growth of weeds (i.e. undesired vegetation). For this purpose, they are normally used in the form of herbicidal compositions (i.e. in association with compatible diluents or carriers suitable for use in herbicidal compositions), for example as hereinafter described.

The compounds of general formula I show herbicidal activity against dicotyledonous (i.e. broad-leafed) and monocotyledonous (e.g. grass) weeds by post-emergence or pre-emergence application. By the term "post-emergence application" is meant application to the aerial or exposed parts of the emerged weeds or to the soil in which they are growing. By the term "pre-emergence application" is meant application to the soil in which the weed seeds or seedlings are present, before the emergence of the weeds above the surface of the soil. For example, the compounds of general formula I may be used to control the growth of weeds such as *Amaranthus* spp., e.g. *A. retroflexus*, *Chenopodium* spp., e.g. *C. album*, *Ipomoea* spp., e.g. *I. purpurea*, *Matricaria inodora*, *Xanthium strumarium*, *Polygonum* spp., e.g. *P. convolvulus*, *P. lapathifolium* and *P. pennsylvanicum*, *Sinapis* spp., e.g. *S. arvensis*, *Solanum* spp., e.g. *S. nigrum*, *Portulaca oleracea*, *Stellaria media*, *Digitaria* spp., e.g. *D. sanguinalis*, *Eleusine* spp., e.g. *E. africana* and *E. indica*, *Poa* spp., e.g. *P annua*, *Echinochloa* spp., e.g. *E. crus-galli* and *Sorghum halepense* by pre- or post-emergence application, *Bidens pilosus*, *Sesbania* spp. and *Datura* spp., e.g. *D. stramonium* by post-emergence application and *Myosotis arvensis*, *Tribulus terrestris*, *Urtica urens*, *Alopecurus myosuroides*, *Avena fatua*, *Bromus tectorum*, *Holcus lanatus* and *Setaria viridis* by pre-emergence application.

The amounts of the compounds of general formula I applied vary with the nature of the weeds, the compositions used, the time of application and (when used to control the growth of weeds in crop-growing areas) the nature of the crop. In general, taking these factors into account, application rates between ¼ lb. and 8 lbs. of active material per acre give good results, particularly with the preferred compounds mentioned hereinafter. However, it must be understood that higher or lower application rates may be used, depending upon the particular problem of weed control encountered.

The compounds of general formula I may be used to control the growth of weeds, for example those species hereinbefore mentioned, by application to a locus of weed infestation which may be an area used for growing crops. Crops of cotton, okra, groundnuts, maize, peas, sugar cane, dwarf beans, French beans and potatoes are particularly well-tolerant of the compounds of general formula I and the use of the latter, by application before sowing of the crop or after showing but before the emergence of the crop above the surface of the soil, for the control of the growth of weeds, for example those species hereinbefore mentioned, in loci of weed infestation which are areas used for growing these crops form a preferred feature of the present invention. Emerged crops of cotton, okra and groundnuts are also particularly well-tolerant of the compounds of general formula I and the use of the latter, by application after the crops have emerged above the surface of soil, for the control of the growth of weeds, for example those species hereinbefore mentioned, in loci of weed infestation which are areas used for growing these crops form another preferred feature of the present invention. The compounds of general formula I may also be used to control the growth of weeds, for example those species hereinbefore mentioned, in loci of weed infestation which are areas containing an emerged crop of maize by directed application, e.g. directional spraying, to the aerial or exposed parts of emerged weeds or the soil in which they are growing or to the soil in which the weed seeds or seedlings are present before emergence of the weeds above the surface of the soil, with avoidance of application of the compounds of general formula I to the emerged crops of maize, and this use forms a further preferred feature of the present invention.

The compounds of general formula I may also be used to control the growth of weeds, especially these indicated above, in established orchards and other tree-growing areas, for example forests, woods and parks, vineyards, plantations, e.g. sugar cane, banana, pineapple and rubber plantations and shrubberies (including areas used for growing fruit-bearing bushes such as black-currants and red-currants), for which purpose they are applied preferably in a directional fashion (e.g. by directional spraying) to the weeds or to the soil in which they are expected to appear, avoiding application to the arborescent plants. The compounds of general formula I may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Suitable methods for applying the compounds of general formula I include:
a. application to the soil surface before the crop is sown or planted;
b. application and shallow incorporation in the soil before the crop is sown or planted;
c. application to the soil surface before the emergence above the surface of the soil of the previously-sown or planted crop;
d. overall application to the crop after its emergence above the surface of the soil;
e. directed application, for example by directed spray, between the rows of annual and permanent crops, for example established orchards and other tree-growing areas, vineyards, plantations and shrubberies as hereinbefore described.

The compounds of general formula I wherein $R^2$ represents an alkoxycarbonyl group are particularly well tolerated by cotton when applied to the surface of the soil or applied and shallowly incorporated in the soil before sowing, when applied to the surface of the soil between sowing and emergence of the crop above the surface of the soil, and when applied after the emergence of the crop above the surface of the soil provided that true leaves have expanded, for example by overall application to the emerged crop, and are also particularly well tolerated by crops of maize, peas, French beans and potatoes when applied before emergence of the crops above the surface of the soil by application to the surface of the soil, and the use of the compounds of general formula I wherein $R^2$ represents an alkoxycarbonyl group for the control of the growth of weeds in loci of weed infestation which are areas used for growing crops of cotton by application before the crop has emerged above the surface of the soil or after true leaves have expanded on the emerged cotton crop or in loci of weed infestation which are areas used for growing crops of maize, peas, French beans and potatoes by application before the crops have emerged above the surface of the soil, form further preferred features of the present invention.

The compounds of general formula I wherein $R^2$ represents a cyano group are particularly well tolerated by crops of groundnuts and potatoes when applied before emergence of the crops above the surface of the soil, for example by application to the surface of the soil or application and shallow incorporation in the soil before sowing or planting or by application to the surface of the soil between sowing or planting and the emergence of the crop above the surface of the soil, and by crops of groundnuts when applied after emergence of the crop above the surface of the soil, for example by overall application to the emerged crop, and the use of the compounds of general formula I wherein $R^2$ represents a cyano group for the control of the growth of weeds in loci of weed infestation which are areas used for growing crops of groundnuts or potatoes by application before the crop has emerged above the surface of the soil and for the control of the growth of weeds in loci of weed infestation which are areas used for growing crops of groundnuts by application after the crop has emerged above the surface of the soil, form further preferred features of the present invention.

The persistence of the compounds of general formula I in the soil is in general sufficient to enable a single application to maintain, by preemergence application as hereinbefore defined, annual crops free from germinating weeds until the crops are well established and able to compete satisfactorily with the weeds. In addition, the herbicidal activity of the compounds of general formula I is not significantly reduced under conditions of heavy rainfall or watering and the compounds are particularly useful for the control of the growth of weeds in crops grown in areas of heavy rainfall, e.g. sugar cane, or in irrigated crops, e.g. cotton, and the use of the compounds of general formula I to control the growth of weeds in loci of weed infestation which are crop-growing areas which are subject to heavy rainfall or watering, for example areas used for growing sugar cane or cotton, form further preferred features of the present invention.

The preferred compounds of general formula I for the control of weeds are compounds of general formula I wherein $R^1$ represents an ethyl, n-propyl, isopropyl or, preferably, methyl group and $R^2$ represents a methoxycarbonyl, n-propoxycarbonyl, isopropoxycarbonyl, n-butoxycarbonyl or, preferably, ethoxycarbonyl group, $R^3$ represents a hydrogen atom and $R^4$ represents an n-propyl, isopropyl, n-butyl, t-butyl, amyl, allyl, cyclopropyl or, preferably, methyl or ethyl group, or wherein $R^1$ represents a methyl group, $R^2$ represents a cyano group and $R^3$ and $R^4$ are the same or different and each represent a methyl or ethyl group. Compounds of particular value for the control of weeds in crops of cotton and groundnuts are 1-(4-ethoxycarbonyl-3-methylisothiazol-5-yl)-3-ethylurea and 1-(4-ethoxycarbonyl-3-methylisothiazol-5-yl)-3-isopropylurea. 1-(4-Ethoxycarbonyl-3-methylisothiazol-5-yl)-3-methylurea is of particular value for the control of weeds in crops of cotton.

Compounds of particular value for the control of weeds in crops of maize are 1-(4-ethoxycarbonyl-3-methylisothiazol-5-yl)-3-methylurea and 1-(4-ethoxycarbonyl-3-methylisothiazol-5-yl)-3-ethylurea. 1-(4-Cyano-3-methylisothiazol-5-yl)-3,3-dimethylurea is of particular value for the control of weeds in crops of groundnuts. 1-(4-Ethoxycarbonyl-3-methylisothiazol-5-yl)-3-isopropylurea, 1-(4-ethoxycarbonyl-3-methylisothiazol-5-yl)-3-methylurea, 1-(4-ethoxycarbonyl-3-methylisothiazol-5-yl)-3-ethylurea, 1-(4-ethoxycarbonyl-3-methylisothiazol-5-yl)-3-n-propylurea and 1-(4-cyano-3-methylisothiazol-5-yl)-3,3-dimethylurea are of particular value for the control of weeds in crops of potatoes.

According to a further feature of the present invention, there are provided compositions suitable for herbicidal use comprising one or more of the isothiazole derivatives of general formula I in association with, and preferably homogeneously dispersed in, one or more compatible herbicidally acceptable diluents or carriers (i.e. diluents or carriers of the type generally accepted in the art as being suitable for use in herbicidal compositions and which are compatible with the compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of compounds of general formula I.

The herbicidal compositions may contain both a diluent or carrier and a surface-active (e.g. wetting, dispersing, or emulsifying) agent. Surface-active agents which may be present in the herbicidal compositions of the present invention may be of the ionic or non-ionic types, for example sulphoricinoleates, quaternary ammonium derivatives, products based on condensates of ethylene oxide with nonyl- or octyl- phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminum silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions, and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions may be ionic or non-ionic (for example of the types described above) and may, when liquid, also serve as diluents or carriers. When desired, liquid compositions of the compounds of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Herbicidal compositions according to the present invention may also contain, if desired, conventional adjuvants such as adhesives, colouring agents and corrosion inhibitors. These adjuvants may also serve as carriers or diluents.

Compositions containing compounds of general formula I, wherein $R^2$ represents an alkoxycarbonyl group, in alkaline conditions are likely to be chemically unstable and are, therefore, generally unsuitable for herbicidal use.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example phenoxyalkanoic acids [e.g. 4-(4-chloro-2-methylphenoxy)-butyric acid, 4-(2,4-dichlorophenoxy)-butyric acid, 2-(4-chloro-2-methylphenoxy)-propionic acid, 2-(2,4-dichlorophenoxy)-propionic acid, 4-chloro-2-methylphenoxyacetic acid, 2,4-dichlorophenoxyacetic acid and 2,4,5-trichlorophenoxyacetic acid], benzoic acid derivatives (e.g. 2,3,6-trichlorobenzoic acid, 2-methoxy-3,6-dichlorobenzoic acid and 3-amino-2,5-dichlorobenzoic acid), halogenated aliphatic acids (e.g. trichloroacetic acid and 2,2-dichloropropionic acid), carbamates [e.g. isopropyl N-(3-chlorophenyl)-carbamate, isopropyl N-phenylcarbamate, and 3-chloro-2-butynyl N-(3-chlorophenyl)-carbamate], thiocarbamates (e.g. S-2,3,3-trichloroallyl N,N-diisopropylthiocarbamate and S-propyl N,N-dipropylthiocarbamate), amides [e.g. 3,4-dichloropropionanilide, 2-chloro-N-isopropylacetanilide and D-N-ethyl-2-(phenylcarbamoyloxy)-propionamide], urea derivatives [e.g. N'-(4-chlorophenyl)-N,N-dimethylurea, N,N-dimethyl-N'-phenylurea, N'-(3,4-dichlorophenyl)-N,N-dimethylurea and N'-(4-chlorophenyl)-N-methoxy-N-methylurea], diazines, (e.g. 5-bromo-3-isopropyl-6-methyl-uracil and 3-cyclohexyl-5,6-trimethyleneuracil), triazines (e.g. 2-chloro-4,6-bis-ethylamino-1,3,5-triazine, 2-chloro-4-ethylamino-6-isopropylamino-1,3,5-triazine and 6-(3-methoxypropylamino)-4-isopropylamino-2-methylthio-1,3,5-triazine), substituted phenols [e.g. 2-methyl-4,6-dinitrophenol, 2-(1-methylpropyl)-4,6-dinitrophenol and 2,4-dichlorophenyl 4-nitrophenyl ether], quaternary ammonium derivatives (e.g. 1,1'-ethylene-2,2'-bipyridylium and 1,1'-dimethyl-4,4'-dipyridylium salts), benzonitrile derivatives (e.g. 2,6-dichlorobenzonitrile and 3,5-diiodo- and 3,5-dibromo-4-hydroxybenzonitriles and their salts and esters e.g. their octanoates), triazole derivatives (e.g. 3-amino-1,2,4-triazole), thiocarbonyl derivatives [e.g. di(methoxythiocarbonyl)disulphide], benzenesulphonylcarbamates (e.g. methyl 4-aminobenzenesulphonylcarbamate, methyl 4-nitrobenzenesulphonylcarbamate and methyl 4-methoxycarbonylaminobenzenesulphonylcarbamate), 4-chloro-2-oxobenzothiazolin-3-ylacetic acid, 2-t-butyl-4-(2,4-dichloro-5-isopropoxyphenyl)-5-oxo-1,3,4-oxadiazole, and 2,6-dinitro-N,N-dipropyl-4-trifluoromethylaniline, insecticides, e.g. naphth-1-yl N- methylcarbamate, and fungicides, e.g. 2,6-dimethyl-4-tridecylmorpholine, methyl N-(1-butylcarbamoylbenzimidazol-2-yl)-carbamate and 1,2-bis-(3-methoxycarbonyl-2-thioureido)benzene. Other biologically active materials which may be included in, or used in conjunction with, the herbicidal compositions of the present invention are plant growth regulators, e.g. maleic hydrazide, N-dimethylaminosuccinamic acid and (2-chloroethyl)trimethylammonium chloride, fertilizers containing nitrogen, potassium and phosphorus and trace elements known to be essential to successful plantlife, e.g. iron, magnesium, zinc, manganese, cobalt and copper.

According to a further feature of the present invention there is provided an article of manufacture comprising at least one of the isothiazole derivatives of general formula I or, as is preferred, a herbicidal composition as hereinbefore described, and preferably a herbicidal concentrate which must be diluted before use, comprising at least one of the isothiazole derivatives of general formula I, within a container for the aforesaid derivative or derivatives of general formula I or herbicidal composition and instructions supplied with the aforesaid container setting out the manner in which the aforesaid derivative or derivatives of general formula I or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastic materials and metal, or sacks. The containers will normally be of sufficient capacity to contain amounts of the isothiazole derivatives or herbicidal compositions sufficient to treat at least one acre of ground to control the growth of weeds therein but will not exceed a size which is convenient for conventional methods of handling. The instructions will preferably be physically associated with the container, for example by being printed directly thereon or on a label or tag affixed thereto. The directions will normally indicate that the contents of the container, after dilution if necessary, are to be applied to control the growth of weeds at rates of application between ¼ and 8 lbs. of active material per acre in the manner and for the purposes hereinbefore described.

The following Examples 1 to 7 illustrate the herbicidal compositions of the present invention. Celite PF is a finely divided synthetic magnesium silicate; Ethylan CP is an octylphenol-polyglycol ether containing 9 glycol units; Atlox 3403 is an anionic/non-ionic blend of anionic alkyl aryl sulphonate and non-ionic polyoxyethylene ether and polyoxyethylene glyceride; Atlox 3404 is an anionic/non-ionic blend of anionic alkyl aryl sulphonates and non-ionic polyoxyethylene alkyl aryl ether; Pendol is a dehydrogenated castor oil; Caromax 15/18 is a petroleum naphtha containing 99% of $C_8$–$C_{10}$ fraction; Belloid TD is a polymethylene bis-naphthol sodium sulphonate; Clarcelflo SAS 132 is an inert solid powdered carrier containing 71% silicon dioxide; Sudan 4 is a red dye; Attapulgite granules are granules of attapulgite clay containing 67% silicon dioxide.

EXAMPLE 1

A wettable powder is formed from:

| | |
|---|---|
| 1-(4-ethoxycarbonyl-3-methylisothiazol-5-yl)-3-methylurea | 50% w/w |
| Celite PF | 47.5% w/w |
| Ethylan CP | 2.5% w/w | by dissolving the Ethylan CP in the minimum volume of acetone, adding the solution obtained to a mixture of the isothiazole derivative and the Celite PF in a blender and blending until the acetone has evaporated. The wettable powder thus obtained may be suspended in water and applied at a rate of 2 lbs. of isothiazole derivative in 40 gallons of water per acre to crops of cotton before emergence of the crop above the surface of the soil, to control the growth of weeds such as *Amaranthus retroflexus*, *Portulaca oleracea*, *Tribulus terrestris*, *Echinochloa crus-galli* and *Digitaria sanguinalis* by pre-emergence application.

EXAMPLE 2

A suspension is formed from:

| | |
|---|---|
| 1-(4-ethoxycarbonyl-3-methylisothiazol-5-yl)-3-methylurea | 25% w/w |
| Atlox 3403 | 5% w/w |
| Atlox 3404 | 5% w/w |
| Pendol | 2.5% w/w |
| Caromax 15/18 | to 100% | by milling the isothiazole derivative to a very fine particle size and then adding the other components. The whole is then macerated at very high speed to obtain uniform distribution.

The suspension thus obtained may be diluted in water and applied at a rate of 2 lbs. of isothiazole derivative in 20 gallons of water per acre to crops of cotton in which true leaves have expanded to control the growth of weeds such as *Bidens pilosus*, *Datura stramonium*, *Amaranthus retroflexus*, *Solanum nigrum*, *Digitaria sanguinalis Eleusine africana* and *Sorghum halepense* by post-emergence application, or at a rate of 2 lbs. of isothiazole derivative in 10 gallons of water per acre to crops of cotton, French beans or potatoes which are about to emerge above the surface of the soil to control the growth of weeds such as *Amaranthus* spp., *Polygonum* spp., *Portulaca oleracea*, *Digitaria* spp. and *Echinochloa* spp. by pre-emergence application.

The suspension may be placed in a suitable container, for example a metal can, in an amount sufficient for the treatment of 1 acre of the crop-growing area, i.e. 8 lbs. of emulsifiable suspension containing 2 lbs. of isothiazole derivative, with associated instructions for use corresponding to the indications set out immediately above, the instructions being preferably printed on the container or on a label or tag affixed to the container.

Similar suspensions may be prepared by replacing the 1-(4-ethoxycarbonyl-3-methylisothiazol-5-yl)-3-methylurea by a corresponding amount of at least one other isothiazole derivative of general formula I, for example 1-(4-ethoxycarbonyl-3-methylisothiazol-5-yl)-3-ethylurea or 1-(4-ethoxycarbonyl-3-n-propylisothiazol-5-yl)-3-methylurea.

EXAMPLE 3

A wettable powder is formed from:

| | |
|---|---|
| 1-(4-cyano-3-methylisothiazol-5-yl)-3,3-dimethyl-urea | 50% w/w |
| Ethylan CP | 2.5% w/w |
| Belloid TD | 5% w/w |
| Clarcelflo SAS 132 | 42.5% w/w | by dissolving the Ethylan CP in the minimum volume of acetone, adding to the acetonic solution to the isothiazole derivative, the Clarcelflo SAS 132 and the Belloid TD in a blender and blending until the acetone has evaporated.

The wettable powder thus obtained may be suspended in water and applied at a rate of 4 lbs. of isothiazole derivative in 20 gallons of water per acre to crops of groundnuts before emergence of the crop above the surface of the soil, to control the growth of weeds such as *Amaranthus* spp., *Portulaca oleracea*, *Bromus tectorum*, *Ipomoea* spp., *Xanthium* spp., and *Eleusine indica* by pre-emergence application.

The wettable powder may be placed in a suitable container, e.g. a cardboard box, in an amount sufficient for the treatment of 1 acre of the groundnut-growing area, i.e. 8 lbs. of wettable powder containing 4 lbs. of isothiazole derivative, with associated instructions for use corresponding to the indications set out immediately above, the instructions being preferably printed on the container or on a label or tag affixed to the container.

Proceeding in a similar fashion but replacing the 1-(4-cyano-3-methylisothiazol-5-yl)-3,3-dimethyl-urea by the corresponding amount of 1-(4-ethoxycarbonyl-3-methylisothiazol-5-yl)-3-methylurea, there is obtained a wettable powder which may be suspended in water and applied at a rate of 3 lbs. of isothiazole derivative in 15 gallons of water per acre to crops of maize before emergence of the crop above the surface of the soil, to control the growth of seedlings of *Amaranthus retroflexus*, *Polygonum pennsylvanicum*, *Portulaca oleracea* and *Digitaria sanguinalis* and to prevent the subsequent germination of seeds of these weed species.

The wettable powder may be placed in a suitable container, e.g. a cardboard box, in an amount sufficient for the treatment of 1 acre of the maize-growing area, i.e. 6 lbs. of wettable powder containing 3 lbs. of isothiazole derivative, with associated instructions for use corresponding to the indications set out immediately above, the instructions being preferably printed on the container or on a label or tag affixed to the container.

Similar wettable powders may be prepared by replacing the 1-(4-cyano-3-methylisothiozol-5-yl)-3,3-dimethylurea by a corresponding amount of at least one other isothiazole derivative of general formula I, for example 1-(4-ethoxycarbonyl-3-methylisothiazol-5-yl)-3-ethylurea or 1-(4-ethoxycarbonyl-3-methylisothiazol-5-yl)-3-isopropylurea.

EXAMPLE 4

A suspension is formed as hereinbefore described in Example 2 but replacing the 1-(4-ethoxycarbonyl-3-methylisothiazol-5-yl)-3-methylurea by the same amount, i.e. 25% w/w, of 1-(4-cyano-3-methylisothiazol-5-yl)-3,3-dimethylurea.

The suspension thus obtained may be diluted in water and applied at a rate of 2 lbs. of isothiazole derivative in 10 gallons of water per acre to crops of groundnuts after emergence of the crop above the surface of the soil, to control by post-emergence application emerged seedlings of weeds such as *Chenopodium* spp., *Datura stramonium*, *Ipomoea purpurea*, *Polygonum* spp., *Sesbania* spp., *Xanthium strumarium* and *Echinochloa* spp.

The suspension may be placed in a suitable container, for example a metal can, in an amount sufficient for the treatment of 1 acre of the groundnut-growing area, i.e. 8 lbs. of suspension containing 2 lbs. of isothiazole derivative, with associated instructions for use corresponding to the indications set out immediately above, the instructions being preferably printed on the container or on a label or tag affixed to the container.

EXAMPLE 5

An emulsifiable concentrate is formed from:

| | |
|---|---|
| 1-(4-ethoxycarbonyl-3-methylisothiazol-5-yl)-3-isopropylurea | 10% w/v |
| Atlox 3403 | 5% w/v |
| Atlox 3404 | 5% w/v |
| xylene | 15% w/v |
| cyclohexanone | to 100% | by dissolving the isothiazole derivative, the Atlox 3403 in a mixture of the xylene and cyclohexanone.

The concentrate obtained may be diluted with water and applied at a rate of 4 lbs. of isothiazole derivative in 20 gallons of water per acre to crops of potatoes before emergence of the crop above the surface of the soil to prevent the germination of seeds of weeds such as *Chenopodium* spp., *Sinapis* spp., *Stellaria media*, *Urtica urens*, *Holcus lanatus*, *Poa annua*, *Solanum nigrum* and *Polygonum* spp.

The concentrate may be placed in a suitable container, e.g. a metal can, in an amount sufficient for the treatment of 1 acre of the potato-growing area, i.e. 40 lbs. of concentrate containing 4 lbs. of isothiazole derivative, with associated instructions for use corresponding to the indications set out immediately above, the instructions being preferably printed on the container or on a label or tag affixed to the container.

Similr concentrates may be prepared by replacing the 1-(4-ethoxycarbonyl-3-methylisothiazol-5-yl)-3-isopropylurea by the corresponding amount of at least one other isothiazole derivative of general formula I, for example 1-(4-n-propyloxycarbonyl-3-methylisothiazol-5-yl)-3-methylurea.

EXAMPLE 6

Granules are formed from:-

| | |
|---|---|
| 1-(4-ethoxycarbonyl-3-methylisothiazol-5-yl)-3-isopropylurea | 5% w/w |
| Sudan 4 | 0.1% w/w |
| Attapulgite granules | 94.9% w/w | by impregnating the granules with the dye and the isothiazole derivative in solution in acetone and evaporating the acetone. Suitably, the granules should pass through a 20-mesh British Standard sieve but not through a 35-mesh British Standard sieve.

The granules obtained may be evenly distributed over and shallowly incorporated in the soil of a cotton-growing area at a rate of 6 lbs. of isothiazole derivative per acre, i.e. 120 lbs. of granules per acre, before the sowing of the cotton crop, to control, by pre-emergence application, the germination of seeds of weeds such as *Amaranthus* spp., *Polygonum* spp., *Echinochloa* spp. and *Sorghum helepense*.

The granules may be placed in a suitable container, e.g. a box of sack, in an amount sufficient for the treatment of 1 acre of the cotton-growing area, i.e. 120 lbs. of granules containing 6 lbs. of isothiazole derivative, with associated instructions for use corresponding to the indications set out immediately above, the instructions being preferably printed on the container or on a label or tag affixed to the container.

EXAMPLE 7

1-(4-Cyano-3-methylisothiazol-5-yl)-3,3-dimethylurea is dissolved in the minimum quantity of aqueous 2N sodium hydroxide solution and the pH adjusted to 10 by the addition of glacial acetic acid.

The concentrate obtained, a solution of the sodium salt of 1-(4-cyano-3-methylisothiazol-5-yl)-3,3-dimethylurea, may be diluted with water, with the addition of Ethylan CP (0.1% w/v of resulting diluted solution), and sprayed onto a potato crop, just before emergence of the crop above the surface of the soil, at a rate of 2 lbs. of isothiazole derivative in 20 gallons of water per acre, to control the growth of seedlings of weeds such as *Chenopodium* spp., *Polygonum* spp., *Sinapis* spp., *Solanum nigrum*, *Stellaria media* and *Poa Annua*.

The concentrate may be placed in a suitable container, e.g. a metal can, in an amount sufficient for the treatment of 1 acre of the potato-growing area, i.e. a quantity containing 2 lbs. of isothiazole derivative, with associated instructions for use corresponding to the indications set out immediately above, the instructions being preferably printed on the container or on a label or tag affixed to the container.

EXAMPLE 8

A concentrate is formed from:-

| | |
|---|---|
| 1-(4-cyano-3-methylisothiazol-5-yl)-3,3-dimethyl-urea | 13.5% w/w |
| triethanolamine | 46% w/w |
| water | to 100% | by dissolving the isothiazole derivative in a mixture of the triethanolamine and water.

The concentrate obtained, a solution of the triethanolamine salt of 1-(4-cyano-3-methylisothiazol-5-yl)-3,3-dimethylurea, may be diluted with water and sprayed onto a potato crop, just before emergence of the crop above the surface of the soil, at a rate of 2 lbs. of isothiazole derivative in 20 gallons of water per acre, to control the growth of seedlings of weeds such as *Chenopodium* spp., *Polygonum* spp, *Sinapis* spp., *Solanum nigrum*, *Stellaria media* and *Poa Annua*.

The concentrate may be placed in a suitable container, e.g. a metal can, in an amount sufficient for the treatment of 1 acre of the potato-growing area, i.e. 15 lbs. of concentrate containing 2 lbs. of isothiazole derivative, with associated instructions for use corresponding to the indications set out immediately above, the instructions being preferably printed on the container or on a label or tab affixed to the container.

According to a feature of the present invention, compounds of general formula I are prepared by the reaction of compounds of the general formula:-

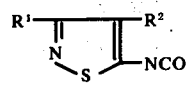

(wherein $R^1$ and $R^2$ are as hereinbefore defined) with compounds of the general formula:-

$$HNR^3R^4 \qquad III$$

(wherein $R^3$ and $R^4$ are as hereinbefore defined), optionally in an inert organic solvent, for example an aromatic hydrocarbon (e.g. toluene) or a halogenated aliphatic hydrocarbon (e.g. chloroform), preferably at 0°–100° C.

Compounds of formula II may be prepared, for example, by the reaction of compounds of the general formula:-

(wherein $R^1$ and $R^2$ are as hereinbefore defined) with a compound of the general formula:-

$$COX_2 \qquad V$$

wherein X represents a bromine, or preferably chlorine, atom. The reaction is preferably carried out in the absence of air and in the presence of an acid, more particularly an acid of the general formula:

$$HX \qquad VI$$

(wherein X is as hereinbefore defined) and an inert organic solvent, for example an aromatic hydrocarbon (e.g. toluene) and at an elevated temperature, for example at a temperature of 60°–110° C.

Compounds of formula IV may be prepared, for example, by the mild alkaine hydrolysis of compounds of the general formula:-

(wherein $R^1$ and $R^2$ are as hereinbefore defined and Ar represents an aryl group, preferably phenyl) or salts thereof, for example the hydrohalide, more particularly the hydrobromide, salts, by treatment with a mild alkali, for example magnesium oxide, magnesium hydroxide or sodium carbonate, in an aqueous organic solvent, for example aqueous dimethylformamide, aqueous ethanol or aqueous acetone, at an elevated temperature, preferably at the reflux temperature of the reaction mixture.

Compounds of formula VII may be prepared, for example, from compounds of the general formula:-

$$NH=CR^1-CHR^2-C(=S)NHCOOAr \text{ or} \qquad VIII$$
$$VIIIa$$
$$NH_2-CR^1=CR^2-C(=S)NHCOOAr \qquad$$
$$VIIIb$$

(wherein $R^1$, $R^2$ and Ar are as hereinbefore defined), the two forms of which may exist in a state of tautomeric equilibrium, by treatment with an oxidising agent, for example iodine in association with a base, preferably pyridine, or sulphuryl chloride or, preferably, bromine in a suitable solvent, for example, ethyl acetate, chloroform, benzene or chlorobenzene, at a temperature below 30° C., preferably at 0°–10° C., or hydrogen peroxide in a suitable solvent, for example, glacial acetic acid. In those instances where bromine or sulphuryl chloride is used as the oxidising agent, the compounds of formula VII so produced may be obtained in the form of their hydrobromide or hydrochloride salts respectively.

Compounds of formula VIII may be prepared, for example, by the reaction of compounds of the general formula:

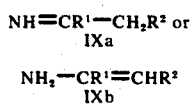     IX
  IXa

NH$_2$—CR$^1$=CHR$^2$
  IXb (wherein R$^1$ and R$^2$ are as hereinbefore defind), the two forms of which may exist in a state of tautomeric equilibrium with compounds of the general formula:-

     X (wherein Ar is as hereinbefore defined) at a temperature of 0°–100° C., preferably 5°–40° C., in an inert organic solvent, preferably acetonitrile, toluene or ethyl acetate.

Compounds of formula X may be prepared by the application or adaptation of known methods.

According to a further feature of the present invention, compounds of formula I wherein R$^2$ represents an alkoxycarbonyl group and R$^1$, R$^3$ and R$^4$ are as hereinbefore defined are prepared by the reaction of compounds of formula IV, wherein R$^2$ represents an alkoxycarbonyl group and R$^1$, R$^3$ and R$^4$ are as hereinbefore defined, with compounds of the general formula:-

     XI wherein R$^4$ is as hereinbefore defined. The reaction is preferably carried out in a polar organic solvent inert to the reactants (preferably pyridine) and at an elevated temperature, preferably at 50°–100° C.

Compounds of formula I may also be prepared by the reaction of compounds of formula VII, or salts thereof as hereinbefore defined, with compounds of formula III, and, in respect of the novel compounds of formula I, this process is a feature of the present invention.

The reaction is preferably carried out at an elevated temperature, for example 50°–100° C., and optionally in the presence of an inert organic solvent, for example an alkanol containing at most 4 carbon atoms (e.g. methanol or ethanol), dimethylformamide, an aromatic hydrocarbon (e.g. benzene) or pyridine.

According to a further feature of the present invention, alkali metal salts and quaternary ammonium salts of compounds of formula I, wherein R$^2$ represents a cyano group, R$^1$, R$^3$ and R$^4$ being as hereinbefore defined, are prepared by the application or adaptation of known methods. The salts are preferably prepared by the reaction together of the said compounds of formula I and an alkali metal hydroxide or alkoxide or an amine, in the presence of an appropriate solvent, for example, water, an alkanol, or a mixture thereof. The salts may optionally be isolated by known methods, for example by crystallisation, if necessary after concentration of the reaction medium or by reduction of the solubility of the salts in the reaction medium, for example, by cooling, by the addition of a poor solvent for the salts (especially where the reaction medium is an alkanol), for example an ether (e.g. diethyl ether), or by the addition of an inert salt formed in theory by the reaction together of the alkali metal or amine and an acid, for example, hydrochloric acid or sulphuric acid (especially where the reaction medium is water).

By the term "known methods" as used in the present specification is meant methods heretofore used or described in the chemical literature.

The compounds of general formula I wherein R$^1$ R$^2$, R$^3$ and R$^4$ are as hereinbefore defined and, when R$^2$ represents a cyano group, their alkali metal salts, and herbicidal compositions comprising them as hereinbefore described form features of the present invention, with the exception of the compounds of general formula I wherein R$^2$ represents an ethoxycarbonyl group, R$^3$ represents a hydrogen atom and:- a. R$^1$ represents a methyl group and R$^4$ represents an ethyl or n-butyl group as such or in association with hexane alone, ethanol alone, aqueous ethanol alone or aqueous ethanol containing sodium ethoxide alone;

b. R$^1$ represents an ethyl group and R$^4$ represents a methyl group as such or in association with ethanol alone, aqueous ethanol alone, water alone or water containing sodium hydroxide alone;

c. R$^1$ represents an n-propyl or isopropyl group and R$^4$ represents a methyl group as such or in association with ethanol alone, water alone, aqueous ethanol alone, or aqueous sodium hydroxide solution alone;

d. R$^1$ and R$^4$ each represent a methyl group as such or in association with ethanol alone or aqueous sodium hydroxide solution alone, such compounds and associations having been previously disclosed in the literature without any disclosure of their herbicidal properties.

The literature also discloses certain associations of the compounds of general formula I wherein R$^2$ represents an ethoxycarbonyl group, R$^3$ represents a hydrogen atom and R$^1$ and R$^4$ are as defined in (a), (b), (c) and (d) above with substances which are not normally suitable for use alone as diluent or carrier in a herbicidal composition, i.e. methylamine, ethylamine or n-butylamine alone or in conjunction with ethanol, aqueous ethanol, dimethylformamide or aqueous dimethylformamide.

The following Examples 9–12 illustrate the preparation of the novel compounds of general formula I and salts thereof, and Examples 13 and 14 illustrate the new process of preparation of the heretofore described compounds of general formula I.

EXAMPLE 9

A solution of isopropylamine in ethanol (33% w/v; 30 ml.) was added, cautiously with swirling, to 4-ethoxycarbonyl-3-methyl-5-phenoxycarbonylaminoisothiazole (prepared according to the method of Goerdeler and Horn, Chemische Berichte, 1963, 96, 1551; 30 g.). When the initial exothermic reaction had subsided the mixture was heated at reflux for 10 minutes, cooled and filtered. The solid was washed with water, and dried to give 1-(4-ethoxycarbonyl-3-methylisothiazol-5-yl)-3-isopropylurea (20.8 g.), m.p. 175°–176° C.

By proceeding in a similar manner, but replacing the isopropylamine by the appropriate amounts of n-propylamine, t-butylamine, n-amylamine, allylamine and cyclopropylamine, there were prepared:-
- 1-(4-ethoxycarbonyl-3-methylisothiazol-5-yl)-3-n-propylurea, m.p. 154°–155° C.,
- 3-t-butyl-1-(4-ethoxycarbonyl-3-methylisothiazol-5-yl)urea, m.p. 215° C.,
- 3-n-amyl-1-(4-ethoxycarbonyl-3-methylisothiazol-5-yl)urea, m.p. 123°–125° C.,
- 3-allyl-1-(4-ethoxycarbonyl-3-methylisothiazol-5-yl)urea, m.p. 125°–127° C., and
- 1-(4-ethoxycarbonyl-3-methylisothiazol-5-yl)-3-cyclopropylurea, m.p. 178°–179° C., respectively.

By again proceeding in a similar fashion, but replacing the 4-ethoxycarbonyl-3-methyl-5-phenoxycarbonylaminoisothiazole and the isopropylamine by the appropriate amounts of 4-cyano-3-methyl-5-phenoxycarbonylaminoisothiazole (prepared according to the method of Goerdeler and Pohland, Chemische Berichte, 1963, 96, 526) and dimethylamine, there was prepared 1-(4-cyano-3-methylisothiazol-5-yl)-3,3-dimethylurea, m.p. 232°–233° C.

EXAMPLE 10

A warm solution of methyl 3-aminocrotonate (prepared according to the method of Conrad and Epstein, Chemische Berichte, 1887, 20, 3054, 10.4 g.) in toluene (20 ml.) was added with stirring to a solution of phenoxycarbonylisothiocyanate (16 g.) in toluene (50 ml.). The temperature of the mixture rose from 20° C. to 30° C. The mixture was then stirred for 1½ hours at ambient temperature, filtered and the solid residue washed with light petroleum (b.p. 40°–60° C.) to give 3-imino-2-methoxycarbonyl-N-phenoxycarbonylthiobutyramide (8.6 g.) in the form of an orange solid, which was then dissolved in ethyl acetate (100 ml.). To this solution, a solution of bromine (1.67 ml.) in ethyl acetate (5 ml.) was added over 15 minutes at 2°–5° C. The mixture was stirred at ambient temperature for 1½ hours and the solid product filtered off to give 4-methoxycarbonyl-3-methyl-5-phenoxycarbonylaminoisothiazole hydrobromide (9.6 g.) m.p. 170°–173° C. A solution of methylamine in ethanol (30% w/v; 20 ml.) was added to 4-methoxycarbonyl-3-methyl-5-phenoxycarbonylaminoisothiazole hydrobromide (9.0 g.). The mixture was heated under reflux for 15 minutes, diluted with water (30 ml.), filtered and the solid residue dried at 100° C., to give 1-(4-methoxycarbonyl-3-methylisothiazol-5-yl)-3-methylurea (4.1 g.), m.p. 236°–237° C.

EXAMPLE 11

A solution of methylamine in ethanol (33% w/v; 50 ml.) was added, cautiously with swirling, to 3-methyl-5-phenoxycarbonylamino-4-n-propoxycarbonylisothiazole hydrobromide (16 g.). When the initial exothermic reaction had subsided, the mixture was heated to reflux for 15 minutes, cooled and filtered. The solid was washed with water, and dried to give 3-methyl-1-(3-methyl-4-n-propoxycarbonylisothiazol-5-yl)urea (7.3 g.), m.p. 191° C.

By proceeding in a similar manner, but replacing the 3-methyl-5-phenoxycarbonylamino-4-n-propoxycarbonylisothiazole hydrobromide by the appropriate amounts of 3-methyl-5-phenoxycarbonylamino-4-isopropoxycarbonylisothiazole hydrobrmoide, 4-n-butoxycarbonyl-3-methyl-5-phenoxycarbonylamnoisothiazole hydrobromide and 3-ethyl-4-methoxycarbonyl-5-phenoxycarbonylaminoisothiazole hydrobromide, there were prepared:
- 3-methyl-1(3methyl-4-isopropoxycarbonylisothiazol-5l -yl)urea, m.p. 194°–195° C.,
- 1-(4-n-butoxycarbonyl-3-methylisothiazol-5-yl)-3-methylurea, m.p. 182°–184° C., and
- 1-(3-ethyl-4-methoxycarbonylisothiazol-5-yl)-3-methylurea, m.p. 188°–190° C. respectively.

By again proceeding in a similar manner, but replacing the 3-methyl-5-phenoxycarbonylamino-4-n-propoxycarbonylisothiazole hydrobromide and methylamine by the appropriate amounts of 4-cyano-3-methyl-5-phenoxycarbonylaminoisothiazole (prepared according to the method of Goerdeler and Pohland, Chemische Berichte, 1963, 96, 526) and diethylamine, there was prepared 1-(4-cyano-3-methylisothiazol-5-yl)-3,3-diethylurea, m.p. 151°–153° C.

The 3-methyl-5-phenoxycarbonylamino-4-n-propoxycarbonylisothiazole hydrobromide, used as a starting material in the above preparation, was prepared as follows:-

A warm solution of n-propyl 3-iminobutyrate (18.2 g.) in toluene (75 ml.) was added to a stirred solution of phenoxycarbonyl isothiocyanate (22.8 g.) in toluene (75 ml.). The temperature of the mixture rose from 20° C. to 35° C. The mixture was then stirred for 1.5 hours at the ambient temperature, filtered and the residue washed with light petroleum (b.p. 40°–60° C.) to give 3-imino-2-n-propoxycarbonyl-N-phenoxycarbonylthiobutyramide (36 g.) in the form of an orange solid. This solid was dissolved in ethyl acetate (125 ml.) and treated at 2°–5° C. with a solution of bromine (0.7 ml.) in ethyl acetate (40 ml.) over 15 minutes. The mixture was stirred at the ambient temperature for 1.5 hours and then filtered to give 3-methyl-5-phenoxycarbonylamino-4-n-propoxycarbonylisothiazole hydrobromide (28 g.), m.p. 157°–163° C.

By proceeding in a similar manner, but replacing the n-propyl 3-iminobutyrate by the appropriate amounts of isopropyl 3-iminobutyrate, n-butyl 3-iminobutyrate and methyl 3-iminovalerate, there were prepared:-
- 3-methyl-5-phenoxycarbonylamino-4-isopropoxycarbonylisothiazole hydrobromide, m.p. 163°–166° C.,
- 4-n-butoxycarbonyl-3-methyl-5-phenoxycarbonylaminoisothiazole hydrobromide, m.p. 132°–133° C., and
- 3-ethyl-4-methoxycarbonyl-5-phenoxycarbonylaminoisothiazole hydrobromide, m.p. 140° C., respectively.

The n-propyl 3-iminobutyrate, used as a starting material in the above preparation, was prepared in the following manner:-

Ammonia gas was passed into a stirred solution of n-propyl acetoacetate (prepared by the method of Fisher, J.A.C.S., 1934, 56, 1766; 72 g.) in diethyl ether (100 ml.) at ambient temperature for 20 hours. The solution was then dried over sodium sulphate, filtered and distilled under reduced pressure to give n-propyl 3-iminobutyrate (18.2 g.), b.p. 114°–118° C./20 mm Hg.

By proceeding in a similar fashion, but replacing the n-propyl acetoacetate by the appropriate amounts of isopropyl acetoacetate and n-butyl acetoacetate there is prepared isopropyl 3-iminobutyrate, b.p. 45°–48° C./0.04 mm Hg, and n-butyl 3-iminobutyrate, b.p. 62° C./0.04 mm Hg, respectively.

The isopropyl acetoacetate, used as a starting material in the above preparation, was prepared as follows:-

A solution of ethyl acetoacetate (250 g.) and concentrated sulphuric acid (10 ml.) in isopropanol (1500 ml.) was heated at reflux for 3 hours. The solvent was removed by distillation, the residue was neutralised by treatment with barium carbonate, filtered and distilled under reduced pressure to give isopropyl acetoacetate (139 g.), b.p. 79°–82° C./20 mm Hg, in the form of a colourless liquid.

By proceeding in a similar fashion but replacing the isopropanol by n-butanol, there was prepared n-butyl acetoacetate, b.p. 92°–98° C./20 mm Hg.

The methyl 3-iminovalerate, used as a starting material in the above preparation of 3-ethyl 4-methoxycarbonyl-5-phenoxycarbonylaminoisothiazole hydrobromide, was prepared as follows:-

Methyl cyanoacetate (99 g.) was added to a stirred solution of ethyl magnesium bromide [prepared by the method well known in the art, from ethyl bromide (328 g.) and magnesium (71 g.)] in diethyl ether, at such a rate that vigorous reflux was maintained. The mixture was then heated at reflux for 40 hours and then treated with a saturated aqueous solution of ammonium chloride (3000 ml.). The ethereal layer was separated off and the aqueous layer was extracted with diethyl ether. The combined ethereal layers were dried over sodium sulphate, the solvent was removed in vacuo, and the residue distilled under reduced pressure to give methyl 3-iminovalerate (33 g.), b.p. 100°–120° C./20 mm Hg.

EXAMPLE 12

A solution of sodium (0.04 g.) in ethanol (2.5 ml.) was added to a solution of 1-(4-cyano-3-methylisothiazol-5-yl)-3,3-dimethylurea (0.5 g.) in warm ethanol (10 ml.). The solution was diluted with diethyl ether (50 ml.) and the precipitate was filtered off to give the sodium salt of 1-(4-cyano-3-methylisothiazol-5-yl)-3,3-dimethylurea (0.3 g.), m.p. above 300° C.

EXAMPLE 13

A solution of 5-amino-4-ethoxycarbonyl-3-methylisothiazole (prepared by the method of Goerdeler and Horn, op cit; 3.72 g.) in pyridine (10 ml.) was treated at 80° C. with methyl isocyanate (1.5 ml.) and the mixture was maintained at 80° C. for 6 hours. The mixture was then poured into an excess of dilute aqueous hydrochloric acid to give an off-white precipitate which was filtered off and recrystallised from ethanol to give colourless crystals of 1-(4-ethoxycarbonyl-3-methylisothiazol-5-yl)-3-methylurea (1.6 g.), m.p. 191°–193° C.

EXAMPLE 14

A suspension of 5-amino-4-ethoxycarbonyl-3-methylisothiazole (9.3 g.) in toluene (100 ml.) was saturated with hydrogen chloride gas at 80° C. The suspension was stirred, heated to reflux and treated with phosgene gas, until a homogenous solution was obtained. The excess of hydrogen chloride was removed with a steam of nitrogen and the solution was cooled to room temperature.

Methylamine gas was passed through the stirred solution for 10 minutes, during which time the temperature rose to 55° C. and the mixture was filtered. On standing the filtrate deposited light brown crystals which were recrystallised from ethanol to give 1-(4-ethoxycarbonyl-3-methylisothiazol-5-yl)-3-methylurea (1.0 g.), m.p. 187°–189° C.

The follow procedures illustrate the preparation of compounds of general formula I heretofore described in the literature as chemical entities or as intermediates in the preparation of other compounds.

PROCEDURE 1

A 50% w/v solution of ethylamine in ethanol (30 ml.) was added to a solution of 4-ethoxycarbonyl-3-methyl-5-phenoxycarbonylaminoisothiazole (prepared according to the method of Goerdeler and Horn, Chemische Berichte, 1963, 96, 1551; 30.6 g.) in warm ethanol (120 ml.). The mixture was heated under reflux for 1 minute, and allowed to cool to ambient temperature and stand for 2 days. The mixture was then heated under reflux for 5 minutes, allowed to cool to ambient temperature and stand for 1 day and poured into cold water (1 liter). The precipitated solid was filtered off, dried and recrystallised from benzene (300 ml.) to give 3-ethyl-1-(4-ethoxycarbonyl-3-methylisothiazol-5-yl)urea (24.8 g.), m.p. 141° C.

By proceeding in a similar fashion, but replacing the ethylamine by the appropriate amounts of methylamine and n-butylamine, there were obtained;- 1-(4-ethoxycarbonyl-3-methylisothiazol-5-yl)-3-methyl urea, m.p. 191°–193° C., and 3-n-butyl-1-(4-ethoxycarbonyl-3-methylisothiazol-5-yl)urea, m.p. 150°–151° C.

PROCEDURE 2

4-Ethoxycarbonyl-5-phenoxycarbonylamino-3-n-propylisothiazole hydrobromide (41.5 g.) was heated at reflux in ethanolic methylamine (33% w/v; 100 ml.) for 15 minutes. The solution was filtered and on cooling deposited white crystals, which were filtered off and washed with water to give 1-(4-ethoxycarbonyl-3-n-propylisothiazol-5-yl)-3-methylurea (18.5 g.), m.p. 173°–174° C.

By proceeding in a similar fashion, but replacing the 4-ethoxycarbonyl-5-phenoxycarbonylamino-3-n-propylisothiazole hydrobromide by the appropriate amounts of 4-ethoxycarbonyl-5-phenoxycarbonylamino-3-isopropylisothiazole hydrobromide and 4-ethoxycarbonyl-3-ethyl-5-phenoxycarbonylaminoisothiazole, there were prepared:-
1-(4-ethoxycarbonyl-3-isopropylisothiazol-5-yl)-3-methylurea, m.p. 206°–208° C., and
1-(4-ethoxycarbonyl-3-ethylisothiazol-5-yl)-3-methylurea, m.p. 189°–190° C., respectively.

4-Ethoxycarbonyl-5-phenoxycarbonylamino-3-n-propylisothiazole hydrobromide, used as a starting material in the above preparation, was prepared as follows:-

A solution of ethyl 3-iminohexanoate (31.4 g.) in toluene (25 ml.) was added to a stirred solution of phenoxycarbonyl isothiocyanate (36 g.) in toluene (75 ml.) at 20° C. The temperature rose to 54° C. The mixture was allowed to cool to room temperature, filtered, and the solid washed with light petroleum (b.p. 40°–60° C.) to give 2-ethoxycarbonyl-3-imino-N-phenoxycarbonylthiohexanamide (62 g.) in the form of a yellow powder. This powder was suspended in ethyl acetate (150 ml.) and treated at 0°–5° C. with a solution of bromine (10.5 ml.) in ethyl acetate (50 ml.) during 20 minutes. The mixture was stirred for a further hour and then filtered, and the solid washed with light petroleum (b.p. 40°–60° C.) to give 4-ethoxycarbonyl-5-phenoxycarbonylamino-3-n-propylisothiazole hydrobromide (69 g.) m.p. 135°–138° C.

By proceeding in a similar manner, but replacing the ethyl 3-iminohexanoate by the appropriate amounts of ethyl 3-imino-4-methylpentanoate and ethyl 3-iminopentanoate, there was prepared 4-ethoxycarbonyl-5-phenoxycarbonylamino-3-isopropylisothiazole hydrobromide, m.p. 114°–115° C., and 4-ethoxycarbonyl-3-ethyl-5-phenoxycarbonylaminoisothiazole, m.p. 83°–85° C., respectively.

I claim:
1. An isothiazole of the formula:

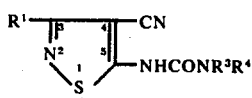

wherein $R^1$ represents a straight or branched-chain alkyl group containing 1 to 3 carbon atoms and $R^3$ and $R^4$ which may be the same or different are each methyl or ethyl or a salt of such an isothiazole with an alkali metal or a herbicidally acceptable strong organic base.

2. An isothiazole as claimed in claim 1 wherein $R^1$ is methyl and $R^3$ and $R^4$ are the same or different and each is methyl or ethyl.

3. An isothiazole as claimed in claim 1 which is 1-(4-cyano-3-methylisothiazole-5-yl)-3,3-dimethylurea.

4. An isothiazole as claimed in claim 1 which is 1-(4-cyano-3-methyl-isothiazole-5-yl)-3,3-diethylurea.

5. A selective herbicidal composition for controlling growth of unwanted plants among crop plants which comprises, as active ingredient, an amount effective to control the growth of said unwanted plants without destroying said crop plants of an isothiazole of the formula:

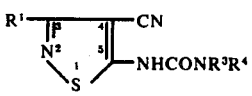

wherein $R^1$ represents a straight or branched-chain alkyl group containing 1 to 3 carbon atoms and $R^3$ and $R^4$ which may be the same or different are each methyl or ethyl or a salt of such an isothiazole with an alkali metal or a herbicidally acceptable strong organic base in association with a compatible herbicidally-acceptable diluent or carrier.

6. A composition according to claim 5 which the said isothiazole is a compound wherein $R^1$ is methyl and $R^3$ and $R^4$ are the same or different and each is methyl or ethyl.

7. A composition according to claim 5 wherein the said isothiazole is 1-(4-cyano-3-methylisothiazol-5-yl)-3,3-dimethylurea.

8. A composition according to claim 5 wherein the said isothiazole is 1-(4-cyano-3-methyl-isothiazole-5-yl)-3,3-diethylurea.

9. A composition according to claim 5 which contains a surface-active agent.

10. A composition acccording to claim 5 in the form of a wettable powder.

11. A composition according to claim 5 in the form of granules.

12. A composition according to claim 5 in the form of an emulsifiable concentrate.

13. A composition according to claim 5 in which the diluent is water.

14. A composition according to claim 5 which contains 0.05% to 90% by weight of the said isothiazole.

15. A composition according to claim 5 which contains another herbicide in addition to the said isothiazole.

16. A composition according to claim 5 which contains, in addition to the said isothiazole, an insecticide, fungicide, plant growth regulator or fertilizer.

* * * * *